(12) United States Patent
George

(10) Patent No.: US 8,465,445 B2
(45) Date of Patent: Jun. 18, 2013

(54) ANKLE AND FOOT ORTHOSIS

(76) Inventor: Patrick George, Canton, MA (US)

(*) Notice: Subject to any disclaimer, the term of this patent is extended or adjusted under 35 U.S.C. 154(b) by 0 days.

(21) Appl. No.: 13/165,424

(22) Filed: Jun. 21, 2011

(65) Prior Publication Data

US 2012/0330206 A1    Dec. 27, 2012

(51) Int. Cl.
 *A61F 5/00* (2006.01)
(52) U.S. Cl.
 USPC .................... 602/23; 602/26; 602/27
(58) Field of Classification Search
 USPC .......... 602/5, 8, 20–28, 60–62; 128/878–879, 128/882
 See application file for complete search history.

(56) References Cited

U.S. PATENT DOCUMENTS

| | | | |
|---|---|---|---|
| 5,219,324 A | 6/1993 | Hall | |
| D358,891 S | 5/1995 | Miller | |
| 5,609,568 A | 3/1997 | Andrews | |
| 5,897,515 A * | 4/1999 | Willner et al. | 602/27 |
| 5,961,477 A | 10/1999 | Turtzo | |
| 6,146,344 A | 11/2000 | Bader | |
| 6,146,349 A | 11/2000 | Rothschild et al. | |
| 6,319,218 B1 | 11/2001 | Birmingham | |
| 6,676,618 B2 | 1/2004 | Andersen | |
| 6,726,645 B1 | 4/2004 | Davis | |
| 6,749,578 B2 | 6/2004 | Peters | |
| 6,827,696 B1 | 12/2004 | Maguire | |
| D501,928 S | 2/2005 | Smits | |
| D503,480 S | 3/2005 | Ingimundarson et al. | |
| 6,860,864 B2 | 3/2005 | Meyer | |
| 6,887,213 B2 | 5/2005 | Smits | |
| 6,945,947 B2 | 9/2005 | Ingimundarson et al. | |
| 7,018,352 B2 * | 3/2006 | Pressman et al. | 602/27 |
| 7,077,818 B2 | 7/2006 | Ingimundarson et al. | |
| 7,270,644 B2 | 9/2007 | Ingimundarson | |
| 7,569,022 B2 | 8/2009 | Morinaka | |
| 2006/0270958 A1 | 11/2006 | George | |

FOREIGN PATENT DOCUMENTS

| | | |
|---|---|---|
| EP | 01108431.6 | 10/1997 |
| EP | 97935923.9 | 10/1997 |
| WO | PCT/SE97/01253 | 7/1997 |
| WO | WO 2004/043289 A2 | 5/2004 |

* cited by examiner

*Primary Examiner* — Michael A. Brown
(74) *Attorney, Agent, or Firm* — Hughes Socol Piers Resnick & Dym, Ltd.; Todd S. Parkhurst (57) ABSTRACT

An orthosis comprising a foot plate, at least one structural frame strut is disclosed. The orthosis frame strut is formed from layered fabric that is infused with a hardened structural resin.

36 Claims, 6 Drawing Sheets

ANKLE AND FOOT ORTHOSIS

SUMMARY OF THE INVENTION

The present invention relates to a custom dynamic carbon fiber Floor Reaction Orthosis (FRO) having anterior cylindrical, or semi-cylindrical, carbon fiber struts; and to an Ankle Foot Orthosis (AFO) having posterior cylindrical, or semi-cylindrical, struts. By a springlike action, these structures control or assist tibial progression during human walking motion. Tibial progression is the forward movement of the leg, in accordance with the invention.

Existing ankle and foot carbon graphite ankle and foot orthoses have flat struts and give unwanted or unnecessary motion. Many orthoses on the market also claim to have a dynamic toe section. The present invention provides the dynamic response necessary to assist patients with their gate deviations, allows them to walk more naturally, and helps the patient to conserve energy.

At mid-stance, the struts of both embodiments of the present invention control the rate of tibial progression. The FRO struts allow the rate of knee flexion to be controlled; and the anterior struts and the flexible footplate receive load as the patient tibial motion progresses. These loaded responses and the corresponding stored energy assist the patient in progressing forward via the stored energy. The AFO loads and stores energy coming into midstance, and also controls the rate of knee flexion. As loading at the toe plate builds, energy is stored to assist in propelling the patient into a swing phase while holding the patient's foot and ankle at the desired angle for toe clearance (typically neutral).

The AFO and the FRO may have custom foot inserts or a natural shoe insert, for example, if there are no foot deformities. Alternatively, a custom foot orthosis may be fabricated addressing accommodative or corrective foot concerns.

The proximal cuff, posterior for the AFO and anterior for the FRO, may have a custom pad. The AFO and FRO may contain padded straps to secure the AFO or FRO to the patients lower leg at the calf posterior (AFO) or upper tibia (FRO). The straps may be secured opposite the cuffs.

A floating cuff design may be used on these orthoses. The floating cuff has pivot points located medially and laterally on the upper ends of the cylindrical struts to follow the path of the tibia in the FRO or in the calf in the AFO as the patient ambulates and the lower leg moves during ambulation. This reduces the pressure over the anterior floor reaction design and the posterior ankle foot orthosis design aspect of the lower leg (tibial crest anterior and gastrocnemius/soleus posterior, respectively). The pivots allow the cuffs to provide total surface pressure as the lower leg moves throughout the gait cycle.

DETAILED DESCRIPTION OF THE INVENTION

Figure 1:
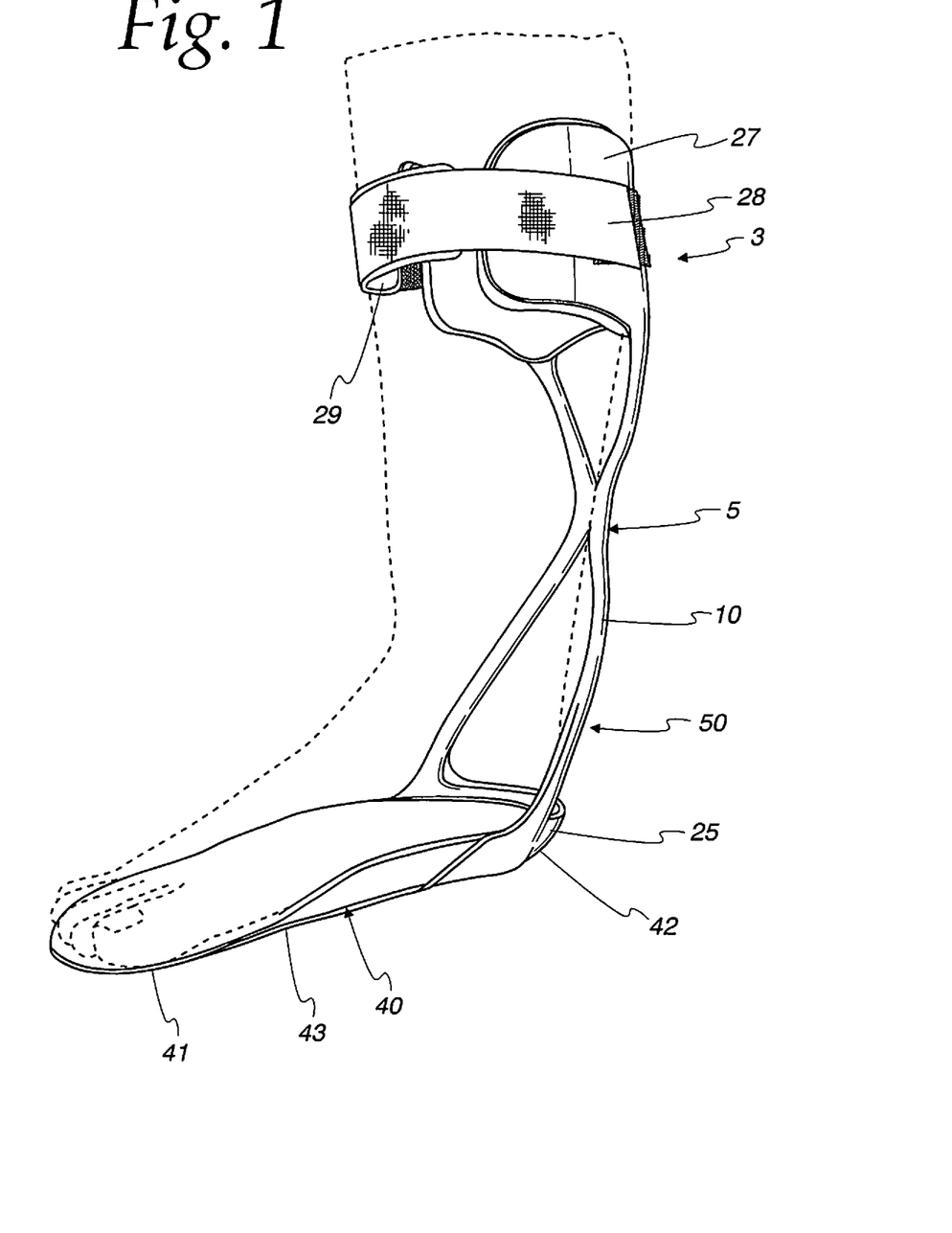
FIG. 1 is a perspective view of an AFO, made in accordance with the invention, shown in an upright position and having a removable bottom foot plate.
Figure 10:
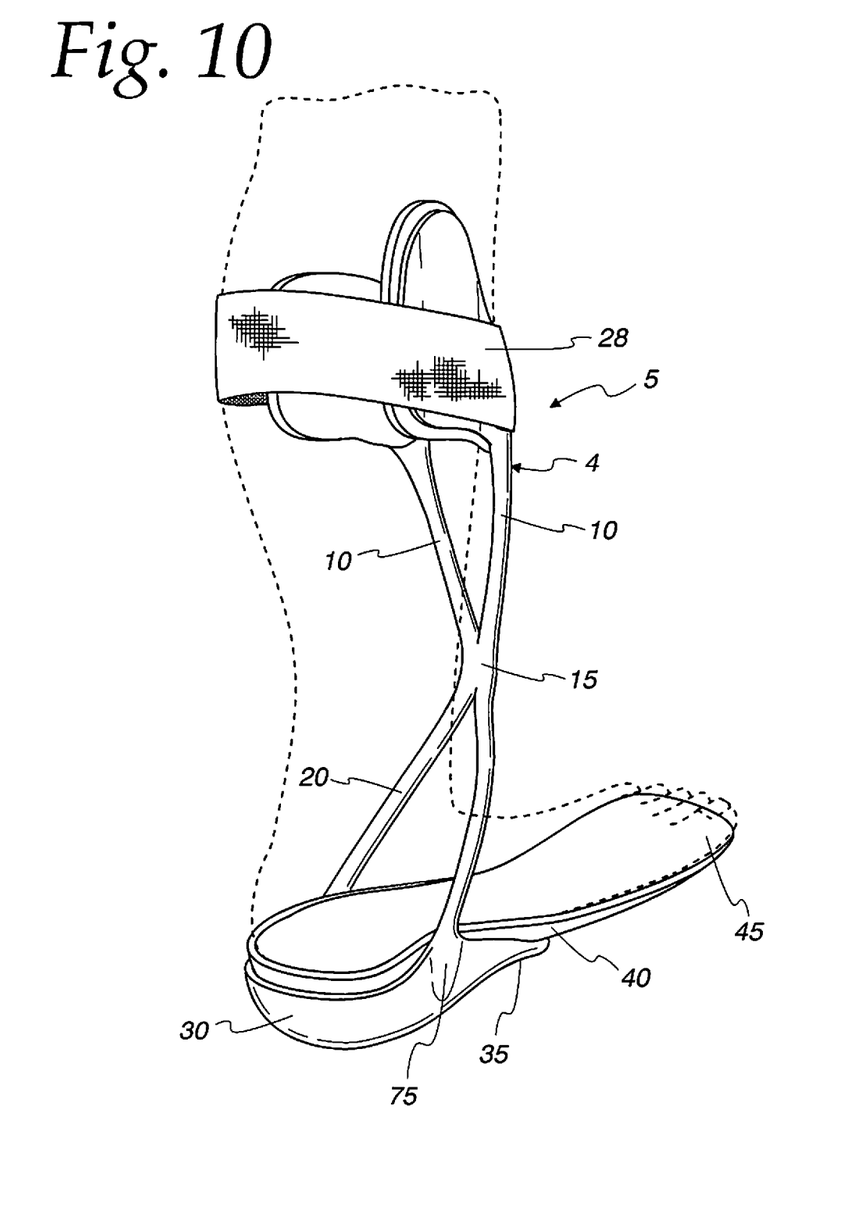
FIG. 10 is a perspective view of the FRO shown in an upright position.
Figure 11:
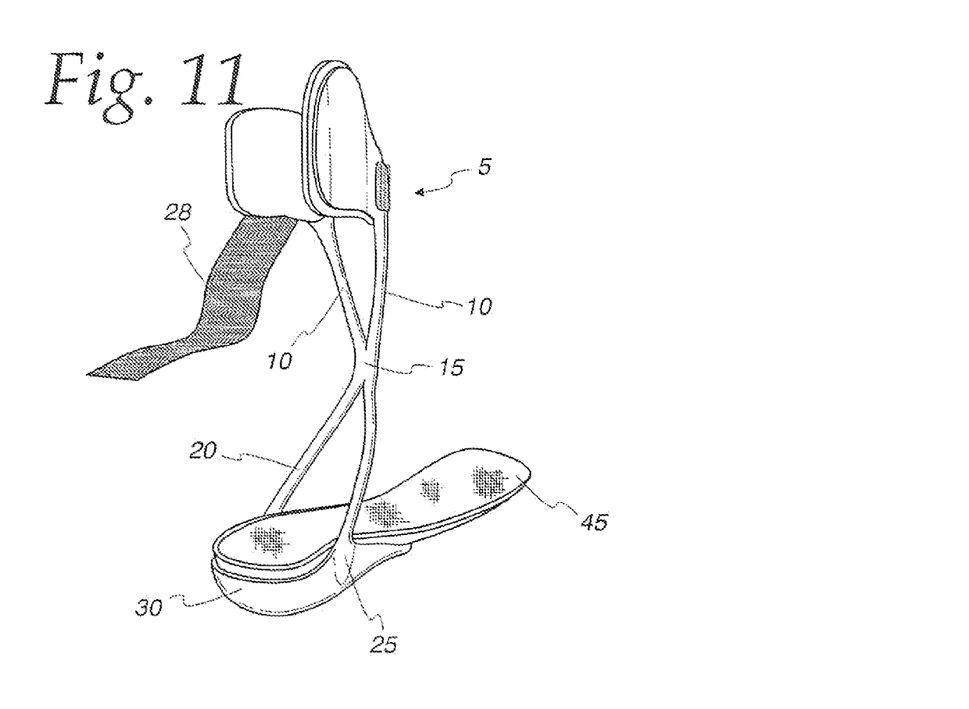
FIG. 11 is a perspective view of the FRO, but with a strap in a loose position.
Figure 12:
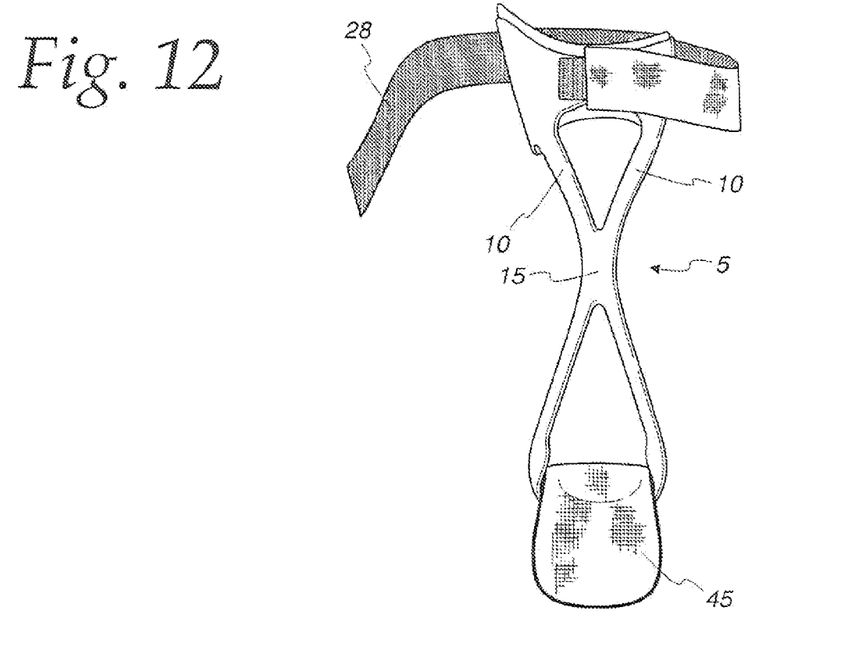
FIG. 12 is a front elevational view of the FRO.

A preferred embodiment of the AFO 3 is shown in FIG. 1a, and a preferred embodiment of the FRO 4 is shown in FIGS. 10-12. The AFO and FRO each generally comprise a structural frame 5 comprised of a laminated construction as described below, and including at least one layer of fabric impregnated with a hardened structural resin or epoxy. The AFO orthosis includes lateral and medial posterior cylindrical or semi-cylindrical struts 10, configured and dimensioned to extend downwardly from below a knee and along the sides of a patient's leg.

The FRO includes lateral and medial anterior cylindrical struts 10 or, alternatively, semi-cylindrical struts. The term "cylindrical" as used here refers to any member having a relatively constant cross-sectional shape. As an example, an "ellipticals strut" has a shape wherein the cross-sectional shape of the strut is elliptical, and vertically-oriented "circular strut" has a circular cross-section.

Figure 2:
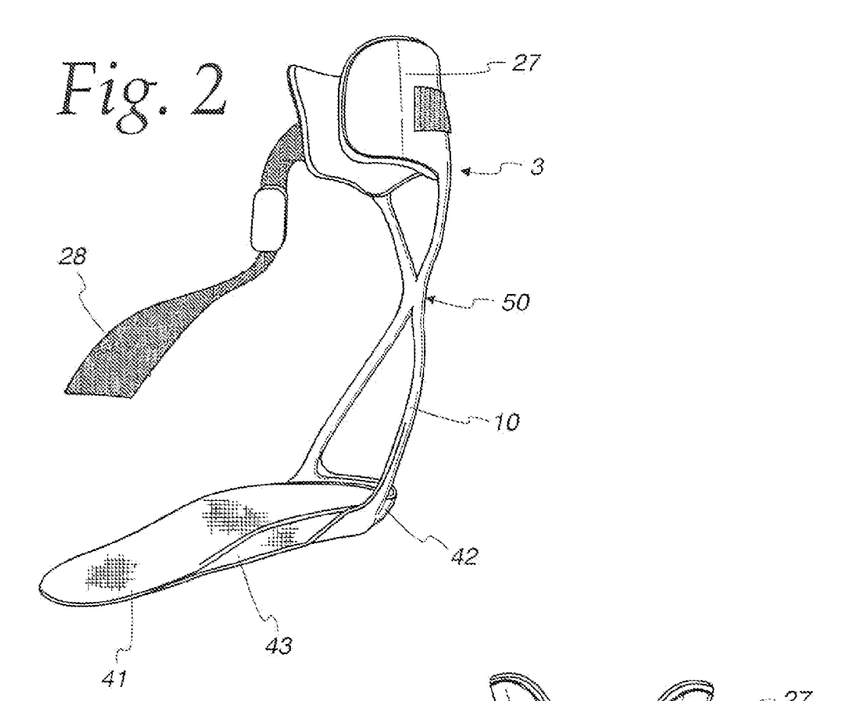
FIG. 2 is a perspective view of the AFO, shown in an upright position and having a removable bottom foot plate and a releasable cuff strap.
Figure 3:
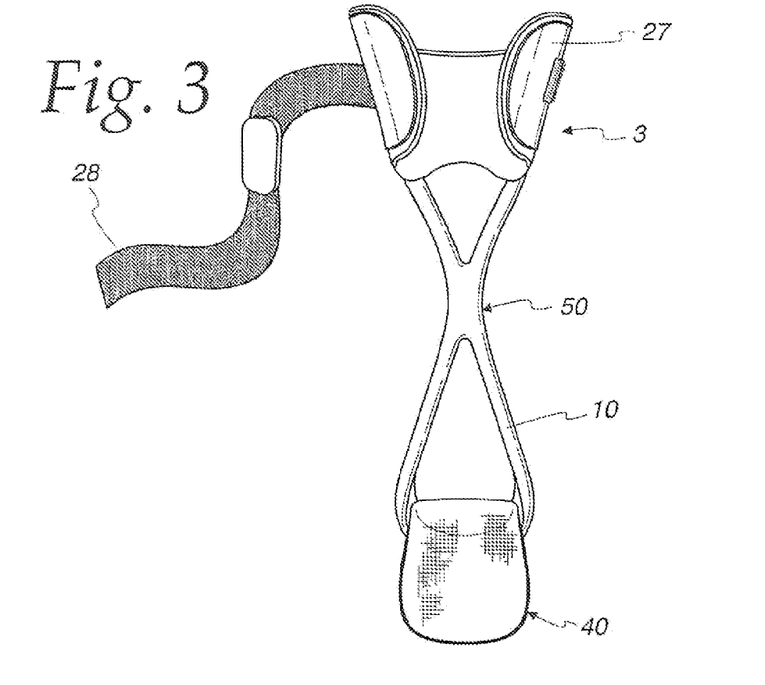
FIG. 3 is a front perspective view of the AFO.
Figure 4:
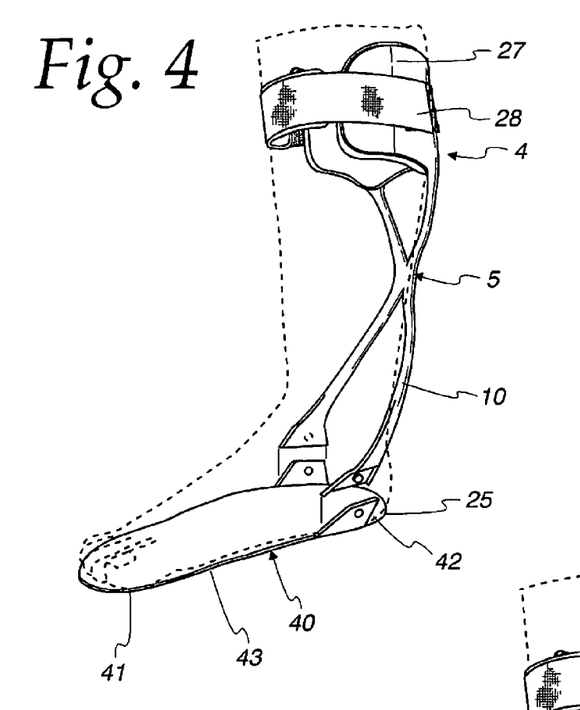
FIG. 4 is a perspective view of the AFO, shown in an upright position and having a modular design including a removable bottom foot plate.
Figure 5:
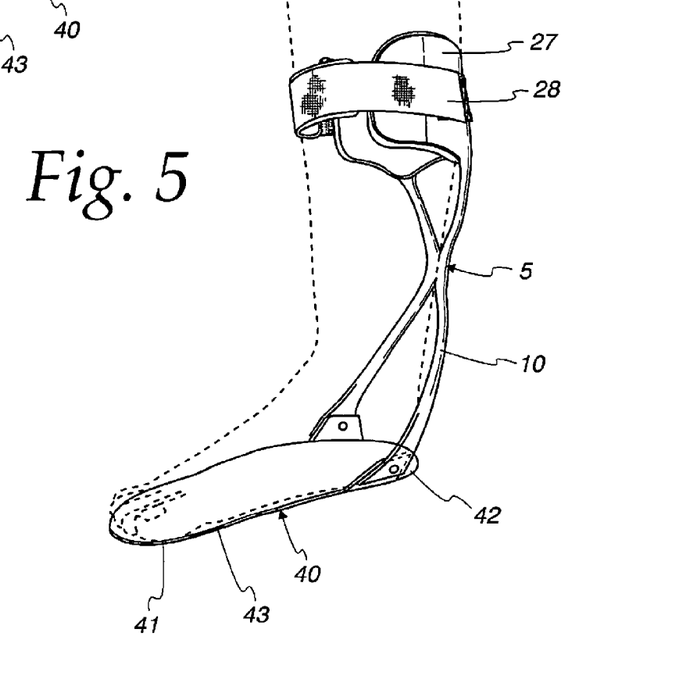
FIG. 5 is a perspective view of the AFO, shown in an upright position and having a removable bottom foot plate and a releasable cuff strap.
Figure 6:
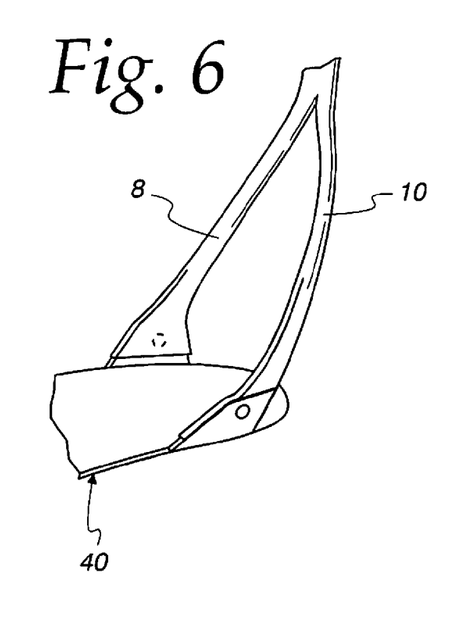
FIG. 6 is a fragmentary perspective view of the AFO.
Figure 7:
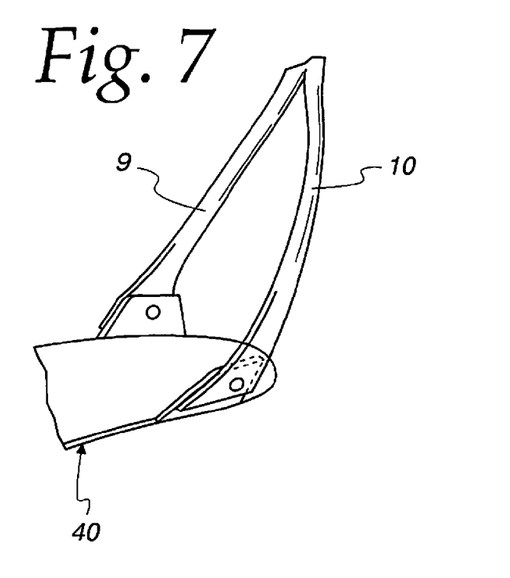
FIG. 7 is a fragmentary view of another embodiment of the AFO.
Figure 8:
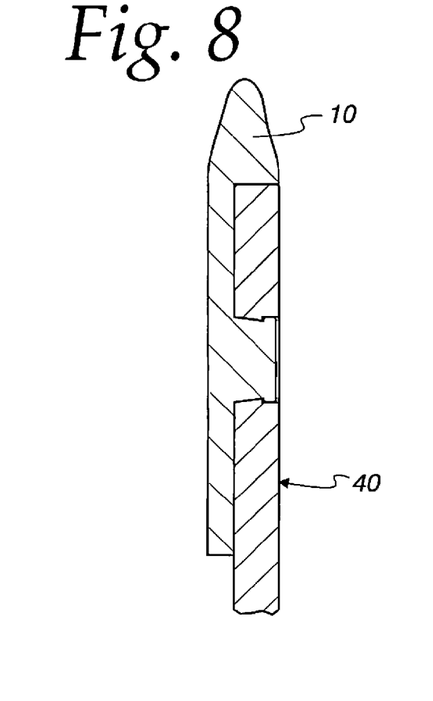
FIG. 8 is a fragmentary sectional view taken substantially in the plane of line 8-8 in FIG. 6.
Figure 9:
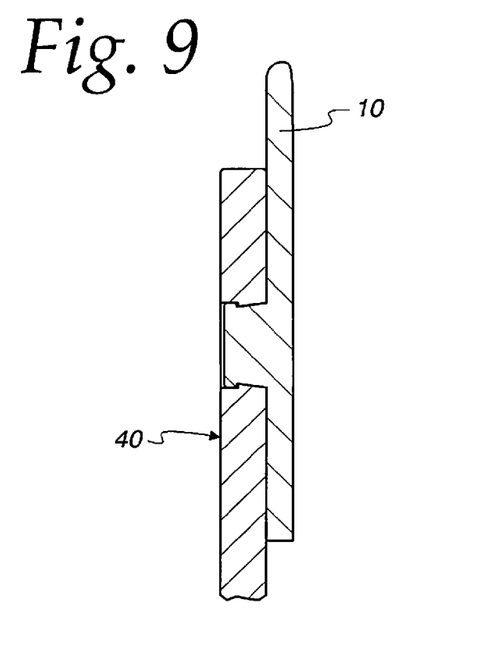
FIG. 9 is a fragmentary sectional view taken substantially in the plane of line 9-9 in FIG. 7.

As shown in the drawings, the lateral and medial struts 10 join in advance of a patient's ankle joint, creating a "Y" configuration between the patient's knee and the joined section 15 of the struts. Immediately below the joined section, the posterior struts are separated to again form the lateral and medial aspects of the struts, thereby forming an inverted "Y" between the joined portion 15 and the lower portion 20. The proximal Y and distal inverted Y are joined in the middle 15 with a fabric, and are impregnated with a resin or epoxy to provide stability with the medial and lateral struts. This allows equal stress loading and unloading of the struts to encourage a relatively natural and fluid gait pattern. As shown in FIG. 2, the bottom splayed ends of the lateral and medial posterior struts are placed at the medial and lateral aspects of the heel section 25. The AFO posterior struts are placed at this part of the foot plate 40 so that, when the patient is at mid-stance, all forces for that leg and orthosis configuration are vertical.

The struts are secured to the foot plate. For example, the foot plate may have slots or female openings to accept the medial and lateral cylindrical struts. Having a female journal member in this orthosis allows the care provider to change the length and the rigidity of the strut or footplate depending upon clinical evaluation.

The medial and lateral posterior struts remain bifurcated over generally one-half the distance from their proximal end to the heel section. The orthosis may contain medial and lateral proximal strut-foot plate pivot points to allow the support members to move in an up and down motion as the leg moves. There is an increase in rigidity and decrease in flexibility of the frame if the strut lengths between the joint 15 and the foot plate 40 are shortened, and conversely, a decrease in rigidity and increase in flexibility if the support members are lengthened. It will be understood that it is within the scope of the present invention to lengthen or shorten the support members in order to gain greater rigidity or flexibility based on clinical necessity and patient anatomy. The lay-up of material, described below, also can be varied in accordance with clinical assessment. The struts may be joined by a carbon tape 15 and formed with a multi direction carbon fabric having at least one layer of fabric.

The struts can be provided as layered carbon fabric constructs for a desired rigidity or flexibility, thereby providing a loading and unloading response throughout all phases of the gait cycle. In other words, the struts have the ability to absorb and return energy, in the manner of mechanical springs thereby creating a dynamic response to changes in orthosis shape or configuration imposed by the wearer's walking or other movement.

To connect the AFO or FRO frame to the leg of the patient, the posterior, or anterior, medial and lateral struts are connected to a proximal cuff 27. That cuff 27 is posterior to the patient's leg for the AFO and anterior for the FRO. Optionally, the cuff may have a custom pad 29. The AFO and FRO may pad straps 28 to secure the AFO or FRO cuff 27 to the patient at the calf posterior (AFO) or upper tibia (FRO). Straps may be secured opposite the cuffs. The cuff 27 may include fastener elements arranged to permit the fastening device to be releasably secured therewith. Furthermore, the cuffs may be "floating," wherein the cuffs are attached to the upper portions of the cylindrical struts, medially and laterally, at pivot points. This floating design allows the cuffs to follow the path of movement of the tibia (in the case of anterior struts) and the path of movement of the calf (in the case of posterior struts) as the patient ambulates and the lower leg moves during ambulation. This reduces pressure along the proximal or distal tibia or calf at the level of the proximal or distal aspect or the cuff along the tibia or calf thorough out the gait cycle.

Medial and lateral cylindrical leg supports or struts may be connected to the orthosis frame. The leg supports or struts may include straps arranged to medially or laterally control the patient's ankle foot region. Although buttons and button holes, snap fasteners, or other similar fasteners commonly used may be employed to connect and secure the straps and cuffs, preferred fasteners include complementary sections of hook-and-loop fastener fabric mounted on opposite overlapping sides of the cuff. The cuff may be constructed from structural materials such as epoxy resin impregnated glass, carbon or aramid fibers, a polymer such as polyethylene or polyurethane, or any other material suitable for an ankle-foot orthosis or FRO design known to one of ordinary skill in the art. The cuff may comprise a textile and padding combination, whether combined with a structural material or taken alone, that is sufficiently rigid to provide support to the patient.

The foot plate 40 is flexible enough so that the heel end can bend slightly in the rear portion thereof. The foot plate is defined by a toe end, a heel end, and an intermediate region or portion between the toe end and the heel end. The relative thickness of the heel end may be greater at regions approaching the intermediate portion. Generally, the foot plate 40 has a curvilinear shape and a uniform or tapered thickness that can increase or decrease from the intermediate region to the heel end and the toe end, depending upon desirability. At midstance, or when the patient reaches a generally flat footed position when the foot plate 40 contacts the ground substantially along its entire length. The compression weight of the patient in this position is continually shifting from the heel end to the toe end of the foot and foot plate in a movement which is called "rollover." The intermediate region 43 of the foot plate maintains a constant thickness along the length thereof to provide a uniform rollover effect.

An alternative embodiment of the invention wherein the heel end 42 of the foot plate 40 bends downward relative to the intermediate region 43. The downward bend provides additional spring and dampening to the heel end 42 during the foot drop of foot slap rollover and heel-off positions. The downward bend delays emergence of the foot condition "flat foot," a condition which occurs when a patient cannot achieve the rigidity of a normal foot and a common early symptom of drop foot. To delay the emergence of flat foot, the foot plate 40 may alternatively be provided with a variable stiffness as opposed to providing a hinge or bend in the foot plate 40. When the patient pushes off the ball and toe regions of the foot at the terminal stance at the "heel off" position, the toe end 41 is subject to large compressive forces and may bend substantially with the foot of the patient to absorb some of the compressive stresses. The relative thickness decreases from the intermediate region 43 to the toe end 41. In the heel-off position, the ankle portion absorbs a majority of the compression generated by the patient, and the foot plate 40 and the ankle portion 50 work to provide dynamic response (the ability to return a certain amount of absorbed energy).

Although the foot plate should cover substantially the length of the foot to provide sufficient control to a patient's gait while distributing pressure from the foot, the foot plate may be in an offset position from a medial or lateral side of the foot so as to generally cover a central portion of the sole of the foot. By offsetting the foot plate, pressure can be relieved from an anterior portion of the leg and the ankle. Furthermore, medial or lateral portions of the foot plate may be removed to achieve the offset position thereof relative to a medial or lateral side of the foot. In addition, portions of the toe end and the heel end may be removed to assist in providing a customized fit of the foot plate in a shoe and to relieve pressure on portions of the orthosis. Optionally, the foot plate may be characterized by a unitary foot and heel construction, and/or an auxiliary ankle construction which permits the flexibility of the orthosis to be selectively determined and easily changed. Furthermore, the footplate portion may be permanently or demountably associated with other parts of the orthosis, whereby the forefoot portion, the heel portion and toe can be readily exchanged with mating heel, forefoot and toe portions. This exchangeability permits size adjustment or accommodation of different spring rates to suit the size of foot of the patient, or the stride and weight of the patient. This modulated and interchangeable form of the footplate allows for a wide range of combinations of spring rate and size to be incorporated into each orthosis. The modular nature of the described foot orthosis also allows one to change and manipulate the desired foot plate length and rigidity.

The struts 10 are secured to the foot plate 40. To aid this connection, the foot plate may have socket and mating tongue constructions to accept the medial and lateral cylindrical struts. Other constructions are shown in FIGS. 4-9. Those skilled in the art will understand that many alternative embodiments of the coupling can be constructed and practiced interchangeably in connection with the many alternative embodiments of the invention. For example, a click mechanism will ensure that the foot plate is secure with the structure of the orthosis and securely attached to the strut(s).

In another embodiment, an orthosis having a single medial or lateral strut is contemplated for use in treating, for example, knee deformities. Knee injuries are a leading cause of long-term disability. Furthermore, many women are susceptible to a knock knee condition (valgus) because of their relatively wider pelvises. Those prone to knee problems are often flat-footed, or whose feet pronat, or turn in too much. A single lateral or medial strut will reduce stress on the knee. The single strut will keep a patient's leg from either falling over into a further abnormal alignment, including knock knee or bow legged (genu valgum or genu varum) patients. The patient's weight is redistributed through the orthosis and over a larger portion of the knee joint, reducing wear-and-tear on the side of the knee that has degenerative changes. The resulting benefits to the patient can be reduced pain, increased activity, and a slowing down of the degeneration of the knee with support.

The surfaces of the cylindrical, or semi-cylindrical struts, which are adjacent to the patient's leg, may include padding material that is pre-fabricated to provide an exact fit to the orthosis, generally having the same profile as the portions of the frame. An instep, medical valgus derotation or lateral varus derotation padded strap may be installed.

The AFO and FRO orthoses can be fabricated using the process of wet lamination or the so-called prepreg process known to those skilled in the art. See generally, PrePrep Technology, Publication No. FGU 017b, March 2009, by Hexcel Corporation, Kent, Washington 98032-1223, which is incorporated by reference herein. See particularly page 22, Properties of Fibre-Reinforced Composites.

The cuff may be releasably connected to the frame or integrated therewith and include additional layers of preimpregnated (prepreg) fabric, bendable layers of molded glass fibers or reformable prepeg material attached to either interior or exterior portions of the frame. Prepreg material can be made via a process of layering a variety of fabrics and rolling the laminate over a mold under high vacuum. For example, prepeg can consist of a combination of a matrix (or resin) and fiber reinforcement. It is available in a unidirectional form wherein there is one direction of reinforcement; and a fabric form, wherein there are several directions of reinforcement. The reinforcement materials impart desirable mechanical properties (i.e.

stiffness, strength, thermal, electric, and chemical properties). The fiber reinforcement can be of any fiber including, but not limited to, high modulus carbon, high strength carbon, E-glass, R-glass, aramid, and polyethylene. The matrix supports the fibers and bonds them in the prepeg composite material. Among the matrix materials which can be employed in the present invention are epoxy, phenolic, and bismaleimide (and polyimide).

The frame strut array is preferably constructed of a plurality of layer of woven glass fibers reinforced with a plastic resin. The woven glass fibers may be reinforced with resin impregnated carbon or aramid fibers in a plastic resin at specific locations of the frame, thereby providing additional structural strength and varying degrees of flexibility. In one embodiment of the invention, the frame is reinforced with multidirectional carbon fibers along the struts, and an array of directionally oriented carbon and spectra-carb fibres depending on desired outcome. In this embodiment, it is preferred that the unidirectional carbon fibers are generally oriented along the longitudinal length of the frame struts. In addition, it is also preferred in this embodiment that a layer of the woven glass fibers are generally oriented at 45 degrees relative to the unidirectional carbon fibers so as to provide optimal strength and flexibility. Alternatively, the struts are reinforced with multidirectional carbon fibers or carbon braids.

It is also preferred that the foot plate be reinforced with a plurality of aramid fibers impregnated with an epoxy matrix to provide additional toughness and flexibility required for durability.

Portions of the frame struts may be constructed from woven glass fibers and the orientation of such fibers may be provided in a predetermined manner. Portions of the orthosis frame struts may include multi-directional oriented carbon fiber. The foot plate may be comprised of at least one layer of spectra carbon fabric. The struts of the orthosis may be reinforced with at least one layer of carbon tape fabric and spectra carb fabric or any other suitable material well known in the art, including aramid fabrics. So-called spectra and carbon provide strength and some flexibility. The foot plate may comprise one or more layers of woven carbon fabric and those layers of woven carbon fabric may be sandwiched between two or more layer of spectra carb fabric.

It will be understood that the frame may be constructed of any suitable material which can provide structural strength to the overall frame. Such materials include, but are not limited to, epoxy resin, kevlar, fiberglass, and spectra carb. It is preferable that the struts do not contact that patient's skin. This preserves skin integrity. To accomplish this, the materials can form a laminate.

It also will be understood that specific regions of the frame may include additional layers of fibers reinforced with a plastic resin to provide greater structural strength at such regions. For example, the medial portion of the frame struts may have a greater thickness than the anterior support members so as to provide a more rigid connection between the foot plate and the ankle portion and to withstand the forces subjected thereto when a patient walks.

It will be further understood that the frame and the foot plate may include other materials, such as fiber glass, silicone, polyurethane coated lycra, polyurethane film, Alkantara and plastic covered textile, as will be apparent to one skilled in the art. Desirable material properties of the frame and the foot plate should possess sufficient resiliency to resist cracking upon application of repeated bending stresses, and ample flexibility to enhance performance characteristics felt by a patient to provide a more natural and dynamic gait while a patient's foot is in functional position.

The orthoses of the present invention can be modulized; i.e., the desired orthosis can be assembled from a variety of different foot plates and support members of various configurations and stiffnesses and sizes. The foot plate and medial lateral portion can be custom shaped to a patient's leg and foot, and the remaining components can be preformed and connected to the custom shaped foot plate and medial lateral portion to form the orthosis of the present invention. Furthermore, the struts of the present invention may be bilateral or unilateral (a single medial or lateral strut), depending upon the needs of the patient.

FRO and AFO Fabrication

The carbon fiber lamination lay-up is made over a modified positive plaster mold which has been made from a patient cast. Fabrication of the FRO and AFO begins by placing a positive plaster mold with pipe into a vacuum system. See the PrePreg Technology publication cited supra and incorporated by reference herein.

The footplate can consist of overlapped unidirectional pre-impregnated fiber placed and compacted over a positive mold. Compaction can be accomplished with a small roller. In this example, the overlapping lay-up is such that four fabric layers run across the mid and hind foot. Plus and minus 45 degree placement of unidirectional pre-impregnated fibers are placed as the first and last layers. All other fiber direction run from heel to toe on the positive mold.

The calf band can be made of several layers of unidirectional pre-impregnated fiber oriented with fibers running from medial to lateral on the positive mold and compacted using a small roller.

The upright section can comprise two pre-impregnated braids double-layered with a unidirectional pre-impregnated fiber core. Upright sections are tied into the calf band and foot plate lay-ups sandwiched or layered into the foot plate lay-up below the calf band lay-up described above. The upright section tie-ins at the foot plate lay-up are reinforced with unidirectional pre-impregnated fiber. The two pre-impregnated unidirectional core-filled braided upright lay in channels from the foot plate below to the calf band above. These channels direct the orientation of the upright such that the two uprights make contact at the mid-section of the mold. The calf band and foot plate sections are wrapped with compaction tape and all three sections (with the calf band, foot plate and mid-section upright) are covered with PVA bagging and placed in a vacuum former prior to and during cure. The cure cycle begins at ambient temperature and increases in a straight slope regime up to 50 degrees below the gel temperature of the material and holds at that temperature for one hour, after which the temperature is increased once again in the same manner up to gel temperature and held for the time requirement to complete the cure. The temp can vary based on manufacturer's specifications for a given resin.

Other parts can be fabricated. Caul plates will be utilized with both the foot plate and calf lay-ups. Foam or solid cores can be provided in place of the unidirectional pre-impregnated fiber core with the braid upright section. The channel for the mid-section of the positive mold can be varied where the braided uprights are positioned.

A technically attractive orthosis can be manufactured according to the following recipe, as elucidated above and in the Pre-Preg Technology publication cited supra:

Foot Section
Mandrel
+/−45 degree
Unidirectional
+/−45 degree
Caul plate
Compaction tape
Calf Section
Optional cosmetic layer
Unidirectional
Optional cosmetic layer
Caul plate
Compaction tape
Upright Section
Mandrel/Mold
Core material inside impregnated braid
Braid ends inter-laid into foot and calf sections
Mold/cal plate
Compaction tape An alternate recipe provides additional plys in the lay-ups:
Foot Section
Mandrel
+/−45 degree
(single)
Unidirectional
(multiple)
Caul plate
Compaction tape
Calf Section
Optional cosmetic payer
Unidirectional
(Multiple)
Optional cosmetic layer
Caul plate
Compaction tape
Upright Section
Mandrel/mold
Core material inside impregnated braid
Braid ends inter-laid into foot and calf sections
Mold/cal plate
Compaction tape The following exemplary orthosis lay-up construction is for a person of approximately 130 lbs. and rated at a functional activity level 3. The U.S. Medicare medical/legal systems provides a functional definition system which indicates how active/and functional people are. Most average people are rated at functional level 3.

The positive mold is made very smooth and a nylon stockinet is tightly placed over the positive mold. A pad is shaped and held in position by a sprayed adhesive. This proximal pad placement and method provides comfort and protection of the proximal tibia calf and will absorb load. A ¼" foam is tapered into the proximal pad simulating a "Y" design and inverted Y design is skived on either side of the tibia. At approximately the median point, the foam pieces are glued together. The glued foam pieces are approximately 1½" in height depending on the height of the patient. Sprayed adhesive secures the foam to the positive mold, starting an inverted "Y" shape. The foam edges end on the medial sustentaculim tali section of the mold, and end laterally on the peroneal arch section of the positive mold. Another nylon is pulled over the positive mold and foam template.

A 6" or 8" PVA bag is moistened in a damp towel for the manufacturer's recommended time period. Then the PVA bag is placed over the mold and secured to the inner vacuum of the system. The vacuum-producing subsystem is then turned on.

The carbon lay-up is made over this PVA bag. Four-inch carbon braid is pulled down over the proximal anterior tibial shell of the floor reaction and proximal posterior for the AFO cuff. Adhesive is sprayed and braid is pulled tightly over the proximal positive mold.

For the foot plate, two pieces of spectra carb are affixed on the mold by adhesive. Then three pieces of carbon fiber weave are adhesively attached to the underlying material. The ends of the cylindrical struts, discussed below, are splayed and sandwiched between the lay-up. A layer of carbon tape can be used to lock in the strut splayed ends. Three more layers of carbon ending at about mid arch and two layers of spectra-carb and/or other desired materials can be used to encapsulate the foot plate lay-up. Additional tapered layers of carbon can be placed along the entire foot plate depending on the desired results of the individual patients needs. The spectra-carb will overlap the carbon fiber strips by about one-quarter inch, all the way around the foot plate. These fabrics should extend to the tapered form ends. Adhesive can be used to secure this lay-up on the positive mold.

The struts are prepared from flexible PVC or welding rod plastic of desired diameter. This rod can be one quarter inch or smaller in diameter, depending on the desired design strength, the patient profile and cylindrical strut stiffness and return. Two pieces of the PVC tube or rod are beveled at all four ends and are laid flat against the proximal shell; and foot plate carbon braid is slid over the PVC tube or welding rod. Nylon thread is tied to the ends of the carbon braid where the beveled PVC tube or welding rod ends. The braid is pulled tight to form a closure of all ends. To make the cylindrical struts more or less flexible/dynamic, this lay-up can be changed in accordance with clinical evaluation and patient data.

A carbon braid is placed over each strut and tied off at the ends; again, leaving the ends of the braid flat and splayed, resulting in two cylindrical carbon struts. The flat splayed ends are sprayed with adhesive and placed on the medial and lateral of the proximal tibia section shell. Carbon tape holds the middle of the struts together creating a "Y" configuration on the top and an inverted "Y" on the bottom. The bottom splayed ends are placed at the medial and lateral aspects of the heel section. These strut ends are sandwiched between two spectra carb layers and three carbon fiber layers. Carbon tape locks the struts on the initial footplate lay-up. Three additional carbon fiber layers are secured and two more pieces of spectra carb are secured to finalize the lay-up. A second layer of 4" cut carbon braid is placed over the proximal section and is secured in place.

This manufacturing method and the constituent parts can be modified to meet patient needs. For example, a more rigid foot plate would control knee motion and stress. Multiple sleeves per strut would increase the strut rigidity.

A second PVA bag can be placed over the lay-up and secured at the bottom of the vacuum system with tape. The top part of the PVA bag is secured with string. A two part resin Epoxy and corresponding hardener can be worked into the lay-up manually and by vacuum.

It will be understood that the above described embodiments of the invention are illustrative in nature, and that modifications to resins, other materials, other parts, fabrication techniques and other methods may occur to those skilled in the art. Accordingly, this invention is not to be regarded as limited to the embodiments disclosed herein.

I claim:

1. An orthosis comprising a foot plate and a structural frame secured to the foot plate, the frame and comprising at least one strut, the strut having an elliptical or circular cross-sectional shape, the strut being formed from multiple layers of fabric infused with a hardened structural resin and having fabric strands oriented at angles to one another.

2. The orthosis of claim 1, wherein the strut is posterior to the leg.

3. The orthosis of claim 1, wherein the strut is anterior to the leg.

4. The orthosis of claim 2, wherein the strut has dynamic loading dynamic response.

5. The orthosis of claim 3, wherein the strut has dynamic loading and unloading responses.

6. The orthosis of claim 1, wherein the orthosis is custom made to a patient profile.

7. The orthosis of claim 1, wherein the orthosis is adjustable to fit more than one patient profile.

8. The orthosis of claim 1 further comprising a fastening device connected to at least one posterior support member at the upper leg engaging portion.

9. The orthosis of claim 1, wherein the foot plate includes a toe end, a heel end, and an intermediate region between the toe end and the heel end.

10. The orthosis of claim 9, wherein the foot plate has a curvilinear shape and thickness which varies from the intermediate region to the heel end and the toe end.

11. The orthosis of claim 2, wherein the orthosis contains medial and lateral pivot points on the struts allowing the posterior support member to move in an up and down motion as the upper leg moves.

12. The orthosis of claim 3, wherein the orthosis contains medial and lateral pivot points on the struts allowing the anterior support member to move in an up and down motion as the upper leg moves.

13. The orthosis of claim 10, wherein the heel end has a shape that corresponds to the anatomical shape of a patient's heel.

14. The orthosis of claim 1, further comprising medial and lateral leg support struts connected to the orthosis frame.

15. The orthosis of claim 14, wherein the lateral and medial supports include a strap arranged to medially control the patient's ankle foot region.

16. The orthosis of claim 14, wherein the lateral and medial supports include a strap arranged to laterally control the patient's ankle foot region.

17. The orthosis of claim 16, wherein the posterior support member struts contain layers of carbon fabric.

18. The orthosis of claim 17, wherein at least one portion of the frame includes multidirectional oriented carbon fiber.

19. The orthosis of claim 1, wherein the cylindrical struts are reinforced with at least one layer of carbon tape fabric and spectra carb fabric.

20. The orthosis of claim 1, wherein the foot plate comprises one or more layers of weave carbon fabric.

21. The orthosis of claim 20, wherein the one or more layers of weave carbon fabric are located between two or more layers of spectra carb fabric.

22. The orthosis of claim 21, wherein the foot plate is comprised of at least one layer of spectra carbon fabric.

23. The orthosis of claim 1, wherein the medial and lateral struts are secured to the foot plate.

24. The orthosis of claim 1, wherein the foot plate has female openings to accept the medial and lateral struts.

25. The orthosis of claim 24, wherein the foot plate length and flexibility is adjusted to patient's need.

26. The orthosis of claim 1, further comprising medial and lateral support members joined to the cylindrical struts at locations approximately equidistant from the foot plate and posterior support members.

27. The orthosis of claim 26, wherein the cylindrical struts are joined by a carbon tape.

28. The orthosis of claim 26, wherein the cylindrical struts are formed with a multi direction carbon fabric having at least one layer.

29. The orthosis of claim 26, wherein the struts are layered so as to achieve a predetermined rigidity or flexibility.

30. The orthosis of claim 26, wherein the struts have a predetermined ability to absorb and return energy.

31. The orthosis of claim 1, wherein the posterior support member comprises at least one reinforcement member integrated into the structural frame at a connection between the struts and medial and lateral portions of the foot plate.

32. The ankle orthosis of claim 31, wherein the at least one reinforcement member comprises at least one layer of fabric structural material.

33. The ankle orthosis of claim 25, wherein the footplate has variable stiffness and loading and unloading properties.

34. The orthosis of claim 1, wherein the struts are cylindrical in cross section.

35. The orthosis of claim 34, wherein the struts are circular cylinders in cross section.

36. The orthosis of claim 34, wherein the struts are elliptical cylinders in cross section.

* * * * *